United States Patent
Crystal et al.

(10) Patent No.: US 10,946,094 B2
(45) Date of Patent: Mar. 16, 2021

(54) ADENOASSOCIATED VIRAL MEDIATED PERSISTANT ANTI-VEGF THERAPY FOR OVARIAN CANCER

(71) Applicant: Cornell University, Ithaca, NY (US)

(72) Inventors: Ronald G. Crystal, New York, NY (US); Arash Rafii Tabrizi, Doha (QA)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/052,697

(22) Filed: Feb. 24, 2016

(65) Prior Publication Data

US 2016/0243229 A1     Aug. 25, 2016

Related U.S. Application Data

(60) Provisional application No. 62/120,163, filed on Feb. 24, 2015.

(51) Int. Cl.

| | |
|---|---|
| *C12N 15/864* | (2006.01) |
| *A61P 35/00* | (2006.01) |
| *A61K 48/00* | (2006.01) |
| *C12N 15/13* | (2006.01) |
| *A61K 39/395* | (2006.01) |
| *C07K 16/22* | (2006.01) |
| *A61K 45/06* | (2006.01) |
| *A61K 31/4745* | (2006.01) |
| *A61K 31/337* | (2006.01) |
| *A61K 39/00* | (2006.01) |

(52) U.S. Cl.
CPC ...... *A61K 39/39558* (2013.01); *A61K 31/337* (2013.01); *A61K 31/4745* (2013.01); *A61K 45/06* (2013.01); *C07K 16/22* (2013.01); *A61K 48/00* (2013.01); *A61K 2039/505* (2013.01); *A61K 2039/54* (2013.01); *C07K 2317/24* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 4,797,368 A | 1/1989 | Carter et al. | |
| 5,464,758 A | 11/1995 | Gossen et al. | |
| 5,814,618 A | 9/1998 | Bujard et al. | |
| 6,342,390 B1 | 1/2002 | Wiener et al. | |
| 6,723,551 B2 | 4/2004 | Kotin et al. | |
| 6,821,511 B2 | 11/2004 | Kotin et al. | |
| 6,884,879 B1 | 4/2005 | Baca et al. | |
| 7,112,715 B2 | 9/2006 | Chambon et al. | |
| 2013/0090375 A1 | 4/2013 | Crystal et al. | |

OTHER PUBLICATIONS

Mingozzi and High, Immune responses to AAV vectors: overcoming barriers to successful gene therapy, (Blood. 2013; 122(1):23-36).*
Ai et al, Adeno-associated virus serotype rh.10 displays strong muscle tropism following intraperitoneal delivery, Scientific Reports, 2017, pp. 1-6.*
Wang et al, Persistent Expression of Biologically Active Anti-HER2 Antibody by AAVrh.10-mediated Gene Transfer, Cancer Gene Ther. Aug. 2010 ; 17(8): 559-570.*
Aravantinos and Pectasides, Bevacizumab in combination with chemotherapy for the treatment of advanced ovarian cancer: a systematic review, Journal of Ovarian Research 2014, 7:57, pp. 1-13.*
Xie et al, AAV-mediated Bevacizumab Maintenance Therapy Inhibits Ovarian Cancer In vivo abstract 727, Molecular Therapy vol. 21, No. 9, e1-46 Sep. 2013.*
Aravantinos et al, A Phase 3 Trial of Bevacizumab in Ovarian Cancer, New England J of Medicine, 2011, 365: pp. 2484-2496.*
Aghajanian et al., Oceans:A Randomized, Double-Blind, Placebo-Controlled Phase III Trial of Chemotherapy With or Without Bevacizumab in Patients With Platinum-Sensitive Recurrent Epithelial Ovarian, Primary Peritoneal, or Fallopian Tube Cancer, *Journal of Clinical Oncology*, 30(17): 2039-2045 (2012).
Ausubel et al., *Current Protocols in Molecular Biology*, Greene Publishing Associates and John Wiley & Sons, NY, (1994) (Table of Contents only).
Avery et al., Intravitreal Bevacizumab (Avastin) for Neovascular Age-Related Macular Degeneration, *Ophthalmology*, 113(3): 363-372 (2006).
Bachelot et al., Randomized Phase II Trial of Everolimus in Combination With Tamoxifen in Patients With Hormone Receptor-Positive, Human Epidermal Growth Factor Receptor 2-Negative Metastatic Breast Cancer With Prior Exposure to Aromatase Inhibitors: A GINECO Study, *Journal of Clinical Oncology*, 30(22): 2718-2724 (2012).
Bantel-Schaal et al., Human Adeno-Associated Virus Type 5 Is Only Distantly Related to Other Known Primate Helper-Dependent Parvoviruses, *Journal of Virology*, 73(2): 939-947 (1999).
Burger et al., Phase II Trial of Bevacizumab in Persistent or Recurrent Epithelial Ovarian Cancer or Primary Peritoneal Cancer: A Gynecologic Oncology Group Study, *Journal of Clinical Oncology*, 25(33): 5165-5171 (2007).
Burger et al., Incorporation of Bevacizumab in the Primary Treatment of Ovarian Cancer, *The New England Journal of Medicine*, 365(26): 2473-2483 (2011).
Carter, Adeno-Associated Virus Vectors in Clinical Trials, *Human Gene Therapy*, 16: 541-550 (2005).
Cearley et al., Transduction Characteristics of Adeno-associated Virus Vectors Expressing Cap Serotypes 7, 8, 9, and Rh10 in the Mouse Brain, *Molecular Therapy*, 13(3): 528-537 (2006).
Chiorini et al., Cloning of Adeno-Associated Virus Type 4 (AAV4) and Generation of Recombinant AAV4 Particles, *Journal of Virology*, 71(9): 6823-6833 (1997).

(Continued)

*Primary Examiner* — Maria Marvich
(74) *Attorney, Agent, or Firm* — Leydig, Voit & Mayer, Ltd.

(57) ABSTRACT

The invention provides a method of treating ovarian cancer in a patient by administering to the patient an adeno-associated virus (AAV) vector encoding an anti-VEGF antibody or antigen binding fragment thereof.

Figure 1:
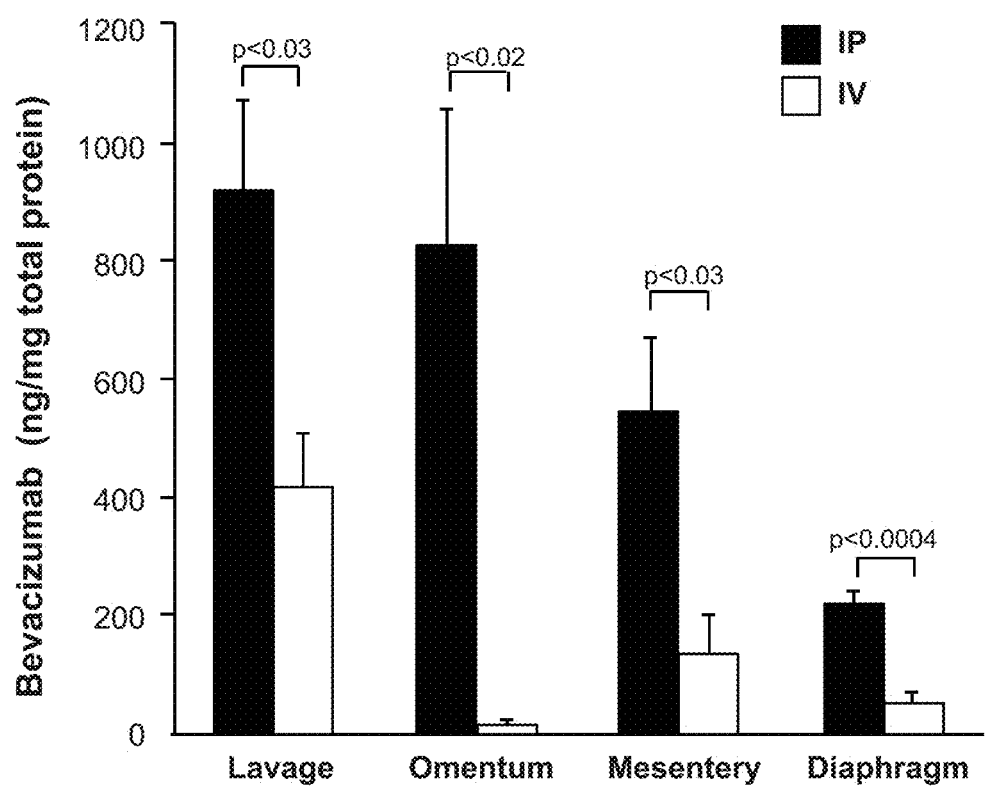

2 Claims, 6 Drawing Sheets
(3 of 6 Drawing Sheet(s) Filed in Color)
Specification includes a Sequence Listing.

(56) References Cited

OTHER PUBLICATIONS

Chiorini et al., Cloning and Characterization of Adeno-Associated Virus Type 5, *Journal of Virology*, 73(2): 1309-1319 (1999).
Daly et al., Neonatal gene transfer leads to widespread correction of pathology in a murine model of lysosomal storage disease, *Proc. Natl. Acad. Sci. U.S.A.*, 96: 2296-2300 (1999).
De et al., High Levels of Persistent Expression of A1-Antitrypsin Mediated by the Nonhuman Primate Serotype rh.10 Adeno-associated Virus Despite Preexisting Immunity to Common Human Adeno-associated Viruses, *Molecular Therapy*, 13(1): 67-76 (2006).
Delord et al., Selective inhibition of HER2 inhibits AKT signal transduction and prolongs disease-free survival in a micrometastasis model of ovarian carcinoma, *Annals of Oncology*, 16: 1889-1897 (2005).
Fang et al., Stable antibody expression at therapeutic levels using the 2A peptide, *Nature Biotechnology*, 23(5): 584-590 (2005).
Ferrara et al., Discovery and Development of Bevacizumab,an Anti-Vegf Antibody for Treating Cancer, *Nature Reviews Drug Discovery*, 3(5): 391-400 (2004).
Flotte, New AAV Serotypes May Broaden the Therapeutic Pipeline to Human Gene Therapy, *Molecular Therapy*, 13(1): 1-2 (2006).
Fuhrmann-Benzakein et al., Inducible and Irreversible control of gene expression using a single transgene, *Nucleic Acids Research*, 28(23): e99 (2000).
Gao et al., Novel adeno-associated viruses from rhesus monkeys as vectors for human gene therapy, *Proc. Natl. Acad. Sci. USA*, 99(18): 11854-11859 (2002).
Gao et al., Clades of Adeno-Associated Viruses are Widely Disseminated in Human Tissues, *Journal of Virology*, 78(12): 6381-6388 (2004).
Gao et al., Biology of AAV Serotype Vectors in Liver-Directed Gene Transfer to Nonhuman Primates, *Molecular Therapy*, 13(1): 77-87 (2006).
Goeddel, Systems for Heterologous Gene Expresssion, *Gene Expression Technology: Methods in Enzymology*, 185:3-7, Academic Press, San Diego, CA. (1990).
Holliger et al., Engineered antibody fragments and the rise of single domains, *Nature Biotechnology*, 23(9): 1126-1129 (2005).
Im et al., The AAV Origin Binding Protein Rep68 is an ATP-Dependent Site-Specific Endonuclease with DNA Helicase Activity, *Cell*, 61: 447-457 (1990).
Indra, et al., Temporarily-controlled site-specific mutagenesis in the basal layer of the epidermis: comparison of the recombinase activity of the tamoxifen-inducible Cre-ER$^T$ and Cre-ER$^{T2}$ recombinases, *Nucleic Acids Research*, 27(22): 4324-4327 (1999).
Jelovac et al., Recent Progress in the Diagnosis and Treatment of Ovarian Cancer, *CA Cancer J. Clin*, 61: 183-203 (2011).
Kramer et al., Transgene Control Engineering in Mammalian Cells, *Methods in Molecular Biology*, 308: 123-144 (2005).
Lambrechts et al., Markers of Response for the Antiangiogenic Agent Bevacizumab, *Journal of Clinical Oncology*, 31(9): 1219-1230 (2013).
Mabuchi et al., Maintenance Treatment with Bevacizumab Prolongs Survival in an In vivo Ovarian Cancer Model, *Clin. Cancer Res.*, 14(23): 7781-7789 (2008).
Mao et al., Persistent Suppression of Ocular Neovascularization with Intravitreal Administration of AAVrh.10 Coding for Bevacizumab, *Human Gene Therapy*, 22: 1525-1535 (2011).
Markman, New developments in the anti-neoplastic drug management of ovarian cancer, *F1000Prime Reports*, 5:48:1-4 (2013).
Niwa et al., Efficient selection for high-expression transfectants with a novel eukaryotic vector, *Gene*, 108: 193-200 (1991).
No et al., Ecdysone-inducible gene expression in mammalian cells and transgenic mice, *Proc. Natl. Acad. Sci.USA*, 93: 3346-3351 (1996).
Pereira et al., The Adeno-Associated Virus (AAV) Rep Protein Acts as both a Repressor and an Activator to Regulate AAV Transcription during a Productive Infection, *Journal of Virology*, 71(2): 1079-1088 (1997).
Perren et al., A Phase 3 Trial of Bevacizumab in Ovarian Cancer, *The New England Journal of Medicine*, 365(26): 2484-2496 (2011).
Presta et al., Humanization of an Anti-Vascular Endothelial Growth Factor Monoclonal Antibody for the Therapy of Solid Tumors and Other Disorders, *Cancer Research*, 57: 4593-4599 (1997).
Remington, The Science and Practice of Pharmacy, 21st Edition, Lippincott Williams & Wilkins, Philadelphia, PA (2001) (Table of Contents only).
Rutledge et al., Infectious Clones and Vectors Derived from Adeno-Associated Virus (AAV) Serotypes Other Than AAV Type 2, *Journal of Virology*, 72(1): 309-319 (1998).
Sambrook et al., Molecular Cloning: A Laboratory Manual, Fourth Edition, Cold Spring Harbor Press, Cold Spring Harbor, NY, (2001) (Table of Contents only).
Siegel et al., Cancer Statistics, 2013, *CA Cancer J. Clin.*, 63:11-30 (2013).
Srivastava et al., Nucleotide Sequence and Organization of the Adeno-Associated Virus 2 Genome, *Journal of Virology*, 45(2): 555-564 (1983).
Sondhi et al., Enhanced Survival of the LINCL Mouse Following CLN2 Gene Transfer Using the rh.10 Rhesus Macaque-derived Adeno-associated Virus Vector, *Molecular Therapy*, 15(3): 481-491 (2007).
Vassileva et al., Effects of sustained and intermittent paclitaxel therapy on tumor repopulation in ovarian cancer, *Mol. Cancer Ther.*, 7(3): 630-637 (2008).
Weis et al., Tumor angiogenesis: molecular pathways and therapeutic targets, *Nature Medicine*, 17(11): 1359-1370 (2011).
Wu et al., Adeno-associated Virus Serotypes: Vector Toolkit for Human Gene Therapy, *Molecular Therapy*, 14(3): 316-327 (2006).
Wu et al., Mutational Analysis of the Adeno-Associated Virus Type 2 (AAV2) Capsid Gene and Construction of AAV2 Vectors with Altered Tropism, *Journal of Virology*, 74(18): 8635-8647 (2000).
Yu et al., The prognostic value of vascular endothelial growth factor in ovarian cancer: A systematic review and meta-analysis, *Gynecologic Oncology*, 128: 391-396 (2013).
Watanabe et al., AAVrh.10-mediated genetic delivery of bevacizumab to the pleura to provide local anti-VEGF to suppress growth of metastatic lung tumors, *Gene Therapy*, 17(8): 1042-1051 (2010).
GenBank Accession Record No. U89790.1, submitted on Feb. 17, 1997.
GenBank Accession Record No. J01901.
GenBank Accession Record No. AF043303.1.
GenBank Accession Record No. AF085716.1.

\* cited by examiner

A.

B. Tumor weight

C. Tumor DNA

A. Time (days)

B.

C.

SEQUENCE LISTING

```
<160> NUMBER OF SEQ ID NOS: 3

<210> SEQ ID NO 1
<211> LENGTH: 369
<212> TYPE: DNA
<213> ORGANISM: Artificial Sequence
<220> FEATURE:
<223> OTHER INFORMATION: Synthetic

<400> SEQUENCE: 1
gaagtgcagc tggtggagtc tgggggaggc ttggtacagc ctgggggtc cctgagactc      60 tcctgtgcag cctctggata cacctttact aactatggca tgaactgggt ccgccaagct    120
ccagggaagg gcctggagtg ggtcggatgg attaatacct atacgggaga acctacttat    180
gcagccgatt ttaaaaggcg attcaccttc tctctagaca ctagcaagag taccgcgtat    240
ctgcaaatga acagtctgag agctgaggac acggccgtgt attattgtgc aaaatatccc    300
cattactacg gtagtagtca ttggtatttt gatgtctggg gccagggaac cctggtcacc    360
gtctcctca                                                             369

<210> SEQ ID NO 2
<211> LENGTH: 321
<212> TYPE: DNA
<213> ORGANISM: Artificial Sequence
<220> FEATURE:
<223> OTHER INFORMATION: Synthetic

<400> SEQUENCE: 2
gatatccaga tgacccagtc cccaagctcc ctgtccgcct ctgtgggcga tagggtcacc      60
atcacctgca cgccagtca ggacatcagc aactatctga ctggtatca acagaaacca    120 ggaaaagctc cgaaagtact gatttacttt accagtagtc tccatagtgg agtcccttct    180
cgcttctctg gatccggttc tgggacggat ttcactctga ccatcagcag tctgcagcca    240
```

| | |
|---|---|
| gaagacttcg caacttatta ctgtcagcag tacagcacgg ttccctggac atttggacag | 300 |
| ggtactaagg tggagatcaa a | 321 |

<210> SEQ ID NO 3
<211> LENGTH: 2161
<212> TYPE: DNA
<213> ORGANISM: Artificial Sequence
<220> FEATURE:
<223> OTHER INFORMATION: Synthetic

<400> SEQUENCE: 3

| | |
|---|---|
| ggtaccacca tggagtttgg actgagctgg gttttccttg ttgctatttt aaaaggtgtc | 60 |
| cagtgtgaag tgcagctggt ggagtctggg ggaggcttgg tacagcctgg ggggtccctg | 120 |
| agactctcct gtgcagcctc tggatacacc tttactaact atggcatgaa ctgggtccgc | 180 |
| caagctccag ggaagggcct ggagtgggtc ggatggatta tacctatac gggagaacct | 240 |
| acttatgcag ccgattttaa aggcgattc accttctctc tagacactag caagagtacc | 300 |
| gcgtatctgc aaatgaacag tctgagagct gaggacacgg ccgtgtatta ttgtgcaaaa | 360 |
| tatccccatt actacggtag tagtcattgg tattttgatg tctggggcca gggaaccctg | 420 |
| gtcaccgtct cctcagcctc caccaagggc ccatcggtct tccccctggc accctcctcc | 480 |
| aagagcacct ctgggggcac agcggccctg ggctgcctgg tcaaggacta cttccccgaa | 540 |
| ccggtgacgg tgtcgtggaa ctcaggcgcc ctgaccagcg gcgtgcacac cttcccggct | 600 |
| gtcctacagt cctcaggact ctactccctc agcagcgtgg tgaccgtgcc ctccagcagc | 660 |
| ttgggcaccc agacctacat ctgcaacgtg aatcacaagc ccagcaacac caaggtggac | 720 |
| aagaaagttg agcccaaatc ttgtgacaaa actcacacat gcccaccgtg cccagcacct | 780 |
| gagctcctgg ggggaccgtc agtcttcctc ttccccccaa acccaaggga caccctcatg | 840 |
| atctcccgga cccctgaggt cacatgcgtg gtggtggacg tgagccacga agaccctgag | 900 |
| gtcaagttca actggtacgt ggacggcgtg gaggtgcata atgccaagac aaagccgcgg | 960 |
| gaggagcagt acaacagcac gtaccgtgtg gtcagcgtcc tcaccgtcct gcaccaggac | 1020 |
| tggctgaatg gcaaggagta caagtgcaag gtctccaaca aagcccctcc cagccccatc | 1080 |
| gagaaaacca tctccaaagc caaagggcag ccccgagaac acaggtgta caccctgccc | 1140 |
| ccatcccggg atgagctgac caagaaccag gtcagcctga cctgcctggt caaaggcttc | 1200 |
| tatcccagcg acatcgccgt ggagtgggag agcaatgggc agccggagaa caactacaag | 1260 |
| accacgcctc ccgtgctgga ctccgacggc tccttcttcc tctacagcaa gctcaccgtg | 1320 |
| gacaagagca ggtggcagca ggggaacgtc ttctcatgct ccgtgatgca tgaggctctg | 1380 |
| cacaaccact acacgcagaa gagcctctcc ctgtctccgg gtagaaagag gcgagcacct | 1440 |
| gtgaaacaga ctttgaattt tgaccttctc aagttggcgg agacgtcga gtccaaccct | 1500 |
| gggcccgata tccagatgac ccagtcccca agctccctgt ccgcctctgt gggcgatagg | 1560 |
| gtcaccatca cctgcagcgc cagtcaggac atcagcaact atctgaactg gtatcaacag | 1620 |
| aaaccaggaa aagctccgaa agtactgatt tactttacca gtagtctcca tagtggagtc | 1680 |
| ccttctcgct tctctggatc cggttctggg acggatttca ctctgaccat cagcagtctg | 1740 |
| cagccagaag acttcgcaac ttattactgt cagcagtaca gcacggttcc ctggacattt | 1800 |
| ggacagggta ctaaggtgga gatcaaacga actgtggctg caccatctgt cttcatcttc | 1860 |
| ccgccatctg atgagcagtt gaaatctgga actgcttctg ttgtgtgcct gctgaataac | 1920 |
| ttctatccca gagaggccaa agtacagtgg aaggtggata acgcccctcca atcgggtaac | 1980 |

```
tcccaggaga gtgtcacaga gcaggacagc aaggacagca cctacagcct cagcagcacc   2040
ctgacgctga gcaaagcaga ctacgagaaa cacaaagtct acgcctgcga agtcacccat   2100
cagggcctga gttcgcccgt cacaaagagc ttcaacaggg gagagtgtta aggactagtg   2160
g                                                                  2161
```

ADENOASSOCIATED VIRAL MEDIATED PERSISTANT ANTI-VEGF THERAPY FOR OVARIAN CANCER

CROSS-REFERENCE TO RELATED APPLICATIONS

This patent application claims the benefit of U.S. Provisional Patent Application No. 62/120,163, filed Feb. 24, 2015, which is incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 4,491 Byte ASCII (Text) file named "723103_ST25 TXT," created on Feb. 23, 2016.

BACKGROUND OF THE INVENTION

Ovarian cancer is the most lethal gynecologic cancer and fifth leading cause of cancer death in the United States (see e.g., Siegel et al., *CA Cancer J. Clin.*, 63: 11-30 (2013)). It is generally asymptomatic in the early stages and no effective screening approach is available. Approximately 75% of women with ovarian cancer when diagnosed are already at an advanced stage with peritoneal dissemination. Current treatment strategies for advanced ovarian cancer include tumor debulking by surgery and chemotherapy with platinum and taxane based regimens (see e.g., Jelovac et al., *CA Cancer J. Clin*, 61: 183-203 (2011)). Despite progress in treatment, the 5 yr survival for advanced ovarian cancer is only 27% (see e.g., Siegel et al. *CA Cancer J. Clin.*, 63: 11-30 (2013)), and the majority of patients eventually develop drug resistance and experience disease recurrence (see e.g., Markman M., *F1000Prime Rep.*, 5:48 (2013)).

One strategy to treat ovarian cancer is inhibition of angiogenesis by administering anti-VEGF antibodies. Angiogenesis is the growth of blood vessels from pre-existing vasculature, a process essential for tumor growth, and is regulated by a number of factors of which vascular endothelial growth factor (VEGF) is key (see e.g., Weis et al., *Nat Med.*, 17: 1359-1370 (2011)). Ovarian cancer patients with high expression of VEGF show poor prognosis and the overexpression of VEGF is associated with poor progression-free survival and overall survival (see e.g., Yu et al., *Gynecol. Oncol.*, 128: 391-396 (2013)).

Bevacizumab (Avastin®) is a humanized monoclonal IgG1 antibody that targets VEGF-A, a member of VEGF family involved in tumor angiogenesis (see e.g., Presta et al., *Cancer Res.*, 57: 4593-4599 (1997)). This antibody prevents activation of VEGF receptors through binding to and neutralizing all active isoforms of VEGF-A. Bevacizumab has been approved by FDA to treat ovarian cancer, metastatic colorectal cancer, non-small cell lung cancer, glioblastoma multiforme and metastatic renal cell carcinoma. Based on encouraging preclinical data on bevacizumab treatment of ovarian cancer (see e.g., Mabuchi et al., *Clin. Cancer Res.*, 14: 7781-7789 (2008)), efficacy of bevacizumab on ovarian cancer has been studied as a single agent or combined with cytotoxic agents in clinical trials. As a single agent to treat patients with recurrent ovarian cancer, bevacizumab is well tolerated and effective with a responsive rate of 21% (see, Burger et al., *J. Clin. Oncol.*, 25: 5165-5171 (2007)). Four randomized trials have assessed the use of bevacizumab in three different clinical studies of ovarian cancer, including primary treatment, platinum-sensitive and platinum-resistant recurrences (see, Perren et al., *N Engl. J. Med.*, 365: 2484-2496 (2011)); Burger et al., *N Engl. J. Med.*, 365: 2473-2483 (2011)); Aghajanian et al., *J. Clin., Oncol.*, 30: 2039-2045 (2012)); and Pujade-Lauraine et al., *J Clin. Oncol.*, 30:[18_suppl] (2012)). All report improved progression-free survival without an effect on overall survival.

One challenge for treatment of ovarian cancer with anti-VEGF antibodies is that the tumor cells constantly express VEGF (see e.g., Lambrechts et al., *J Clin. Oncol.*, 31: 1219-1230 (2013)), and anti-VEGF therapy withdrawal can result in revascularization. Maintenance bevacizumab treatment has better efficacy with acceptable toxicity in clinical trials (see e.g., Perren et al., *N Engl. J. Med.*, 365: 2484-2496 (2011)); Burger et al., *N Engl. J. Med.*, 365: 2473-2483 (2011)), but requires repetitive bevacizumab therapy.

Therefore, there is a need to develop alternative compositions and methods to administer anti-VEGF antibodies, such as bevacizumab, to treat ovarian cancer. This invention provides such methods. This and other advantages of the invention will become apparent from the detailed description provided herein.

BRIEF SUMMARY OF THE INVENTION

The invention provides a method of treating ovarian cancer in a patient by administering to the patient an adeno-associated virus (AAV) vector encoding an anti-VEGF antibody or antigen binding fragment thereof.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

FIG. 1 is a graph of the local expression of bevacizumab in the peritoneal cavity of Balb/c mice (n=4 or 5) following intraperitoneal (IP) or intravenous administration (IV) of AAVrh10.BevMab. Peritoneal lavage, omentum, mesentery and diaphragm were collected 9 weeks after treatment, and bevacizumab levels were assayed by ELISA and normalized by total protein.

Figure 2:
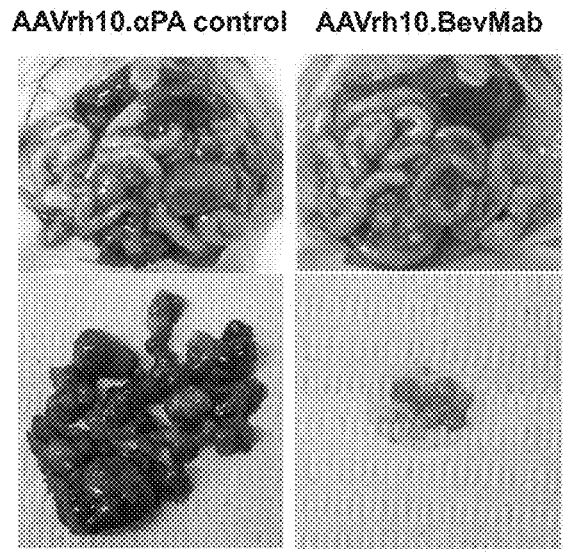
Figure 2:
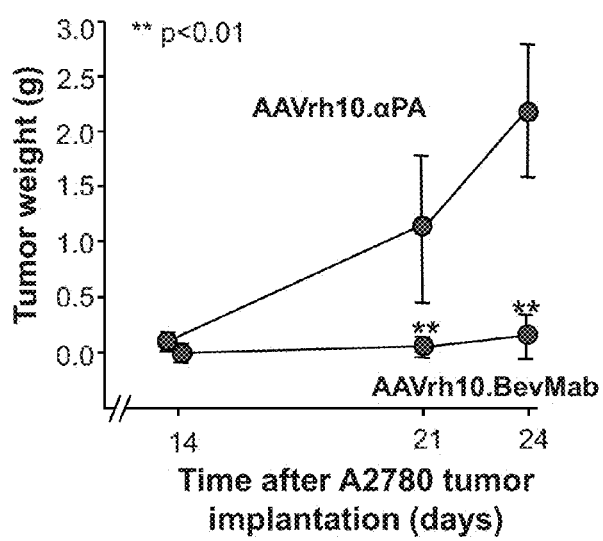
Figure 2:
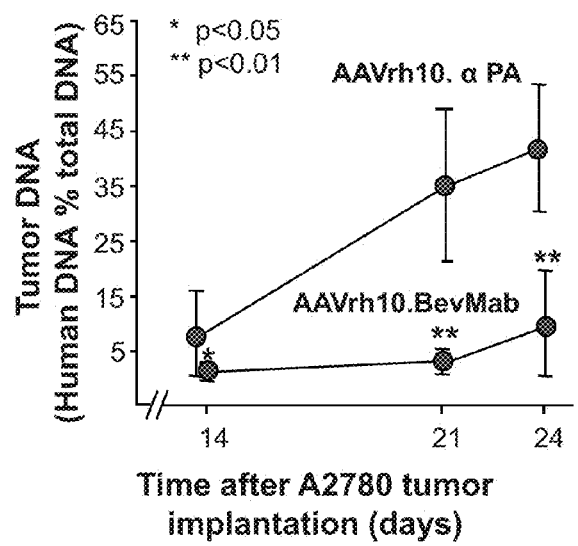

FIG. 2 depicts the results of experiments analyzing the effect of AAVrh10.BevMab treatment on ovarian cancer peritoneal carcinomatosis in mice with xenografts of human ovarian cancer cells. One day after tumor cell inoculation, mice were treated with $10^{11}$ gc AAVrh10.BevMab or a control AAVrh10. vector coding for an irrelevant IgG antibody (AAVrh10.αPA). Panel (A) of FIG. 2 provides images of peritoneal carcinomatosis in mice treated with AAVrh10.αPA (left column) or AAVrh10.BevMab (right column) 24 days after tumor cell inoculation. Panel (B) of FIG. 2 is a graph of the total tumor weight of tumor nodules isolated from the peritoneal cavity of mice treated with AAVrh10.αPA or AAVrh10.BevMab at day 14, 21, and 24 after tumor cell inoculation. Panel C of FIG. 2 is a graph of the amount of tumor DNA isolated from all tissues and organs of mice treated with AAVrh10.αPA or AAVrh10.BevMab at day 14, 21, and 24 after tumor cell inoculation. Data (means±standard error) was obtained from n=10 mice. AAVrh.10BevMab vs. AAVrh10.αPA, *p<0.05, **p<0.01.

Figure 3:
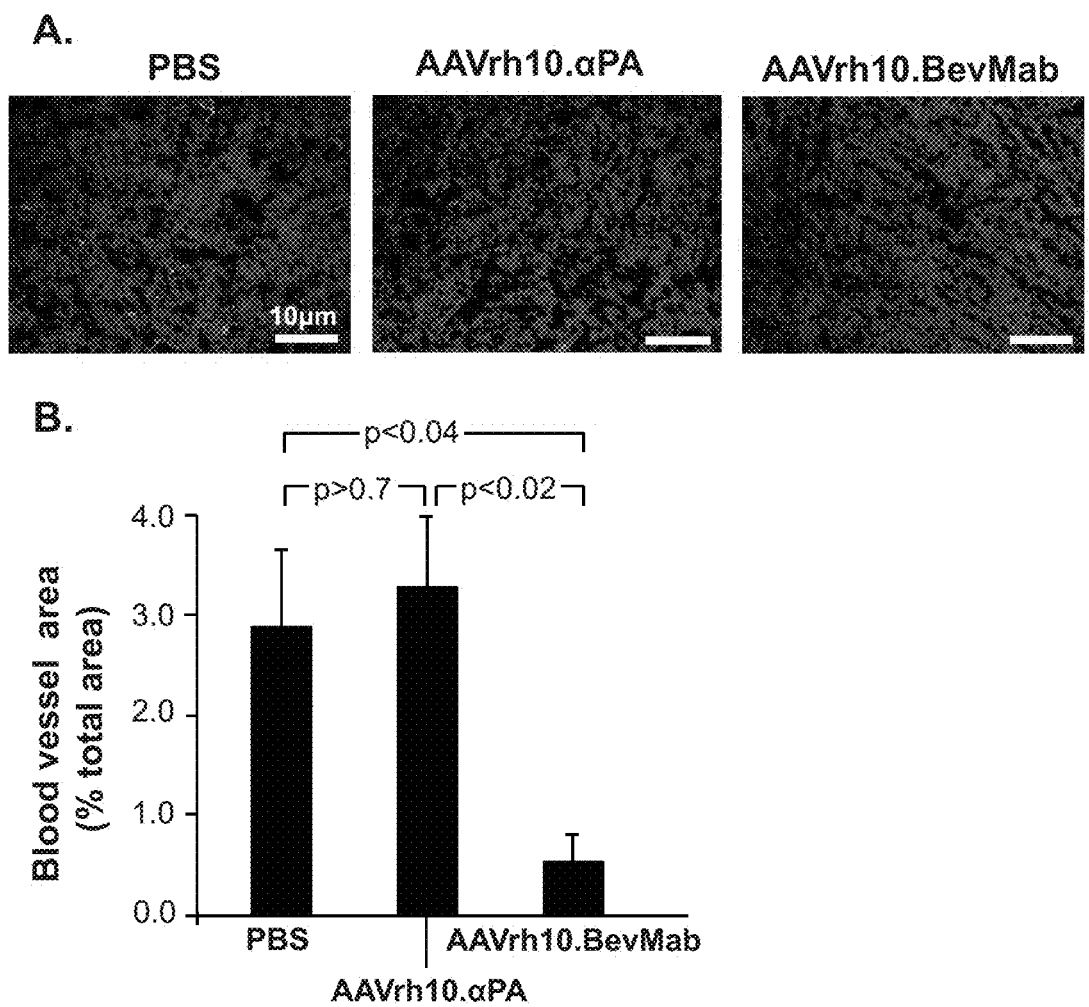

FIG. 3 depicts the results of experiments analyzing the effect of AAVrh10.BevMab treatment on angiogenesis of ovarian cancer. One day after ovarian cancer cell inoculation, mice were treated with $10^{11}$ gc AAVrh10.BevMab, AAVrh10.αPA (control AAV vector) or PBS. On day 24, tumor nodules were collected. Frozen sections were stained with rat anti-mouse CD31 followed by goat anti-rat IgG conjugated with cy3. Nuclei were stained with DAPI. Panel (A) of FIG. 3 depicts images of CD31+ tumors (marker of angiogenesis) for PBS control (left image), AAVrh.10αPA control (center image) or AAVrh.10BevMab (right image) treated mice. Panel (B) of FIG. 3 is a graph of the blood vessel area for each treatment group. Data were obtained from n=4 mice per group.

Figure 4:
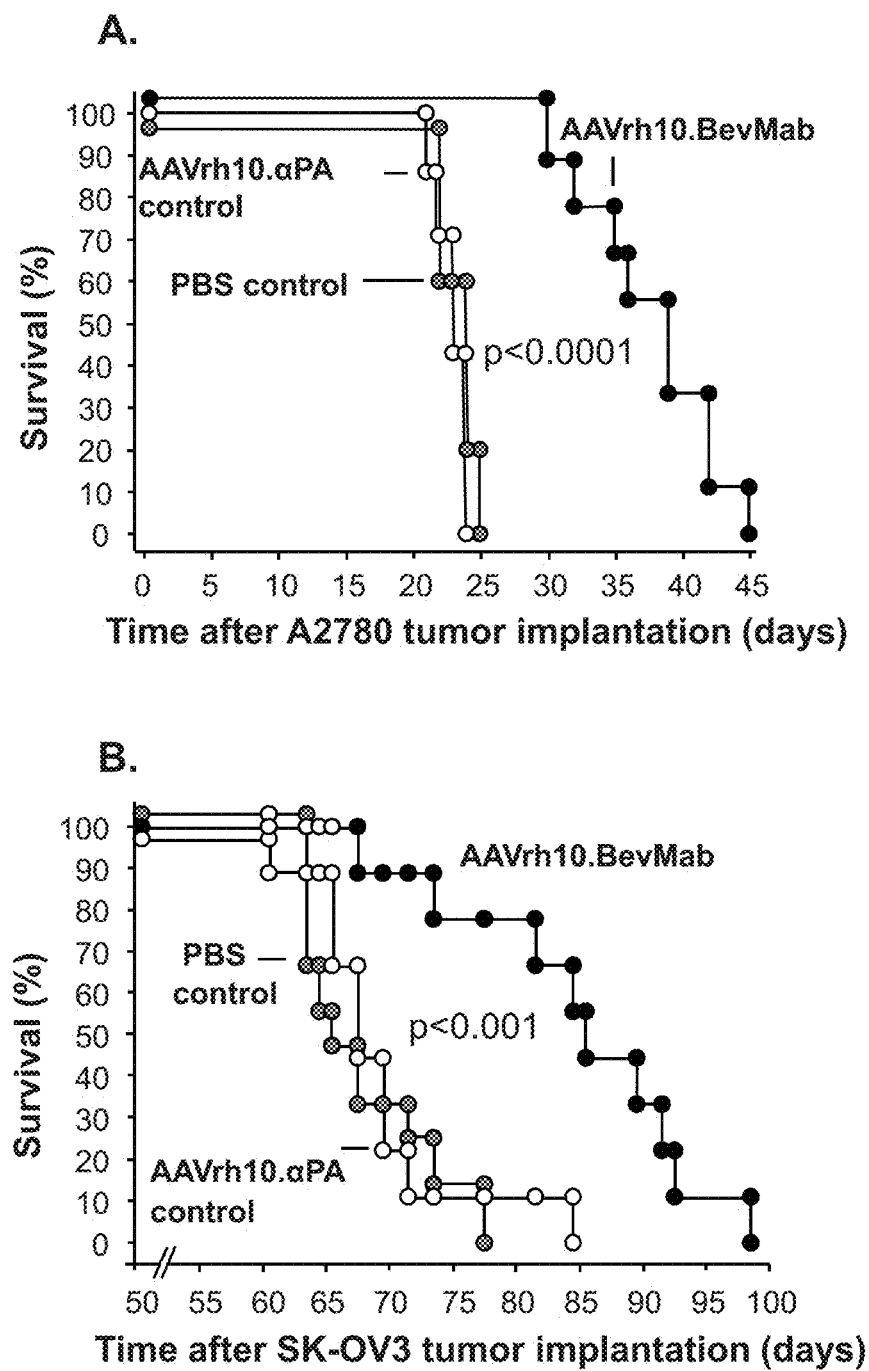

FIG. 4 depicts the results of experiments analyzing the effect of AAVrh10.BevMab on survival of ovarian cancer-bearing mice. One day after ovarian cancer cell inoculation, mice were treated with $10^{11}$gc AAVrh10.BevMab, AAVrh10.PA (control AAV vector) or PBS. Data were obtained from n=7 to 10 animals per group. Panel (A) of FIG. 2 is a graph of the percentage of animals surviving over time for animals inoculated with A2780 ovarian cancer cell tumors, p<0.0001; and Panel (B) is a graph of the percentage of animals surviving over time for animals inoculated with SK-OV3 ovarian cancer cell tumors p<0.001.

Figure 5:
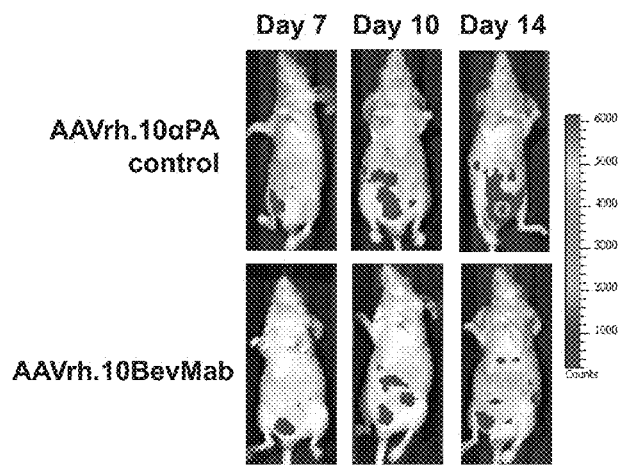
Figure 5:
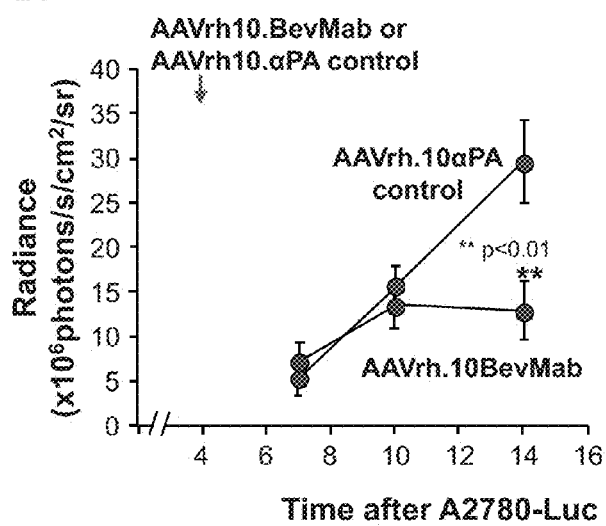
Figure 5:
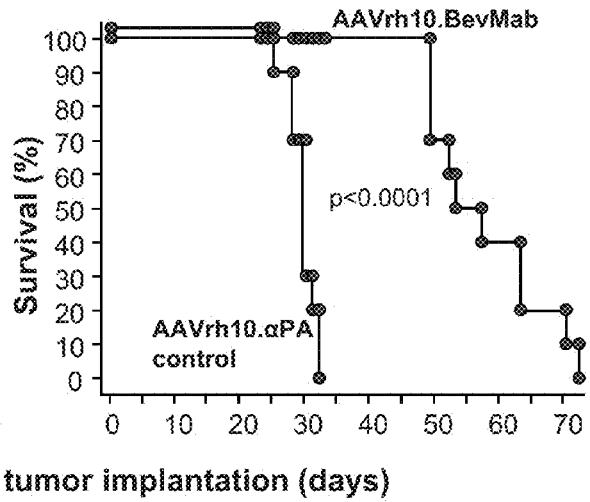

FIG. 5 depicts the results of experiments analyzing the effect of AAVrh10.BevMab on mice with established A2780-luciferase ovarian cancer cell xenografts. A2780-Luciferase cells were administered intraperitoneally into Balb/c nude mice (n=10). Four days after tumor cell inoculation, mice were treated with $10^{11}$ gc AAVrh10.BevMab or AAVrh10.αPA control AAV vector. Tumor growth was assayed by luciferase activity. Panel (A) of FIG. 5 provides images of AAVrh.10 PA control and AAVrh.10BevMab treated mice showing tumor growth on day 7, 10 and 14. Panel (B) of FIG. 5 is a graph of the quantified luciferase activity as a measure of tumor growth of AAVrh.10BevMab treatment mice compared to AAVrh10.αPA treated mice, **p<0.01. Panel (C) of FIG. 5 is a graph a graph of the percentage of mice surviving over time in an AAVrh.10BevMab treatment group and AAVrh10.αPA treatment group, p<0.0001.

Figure 6:
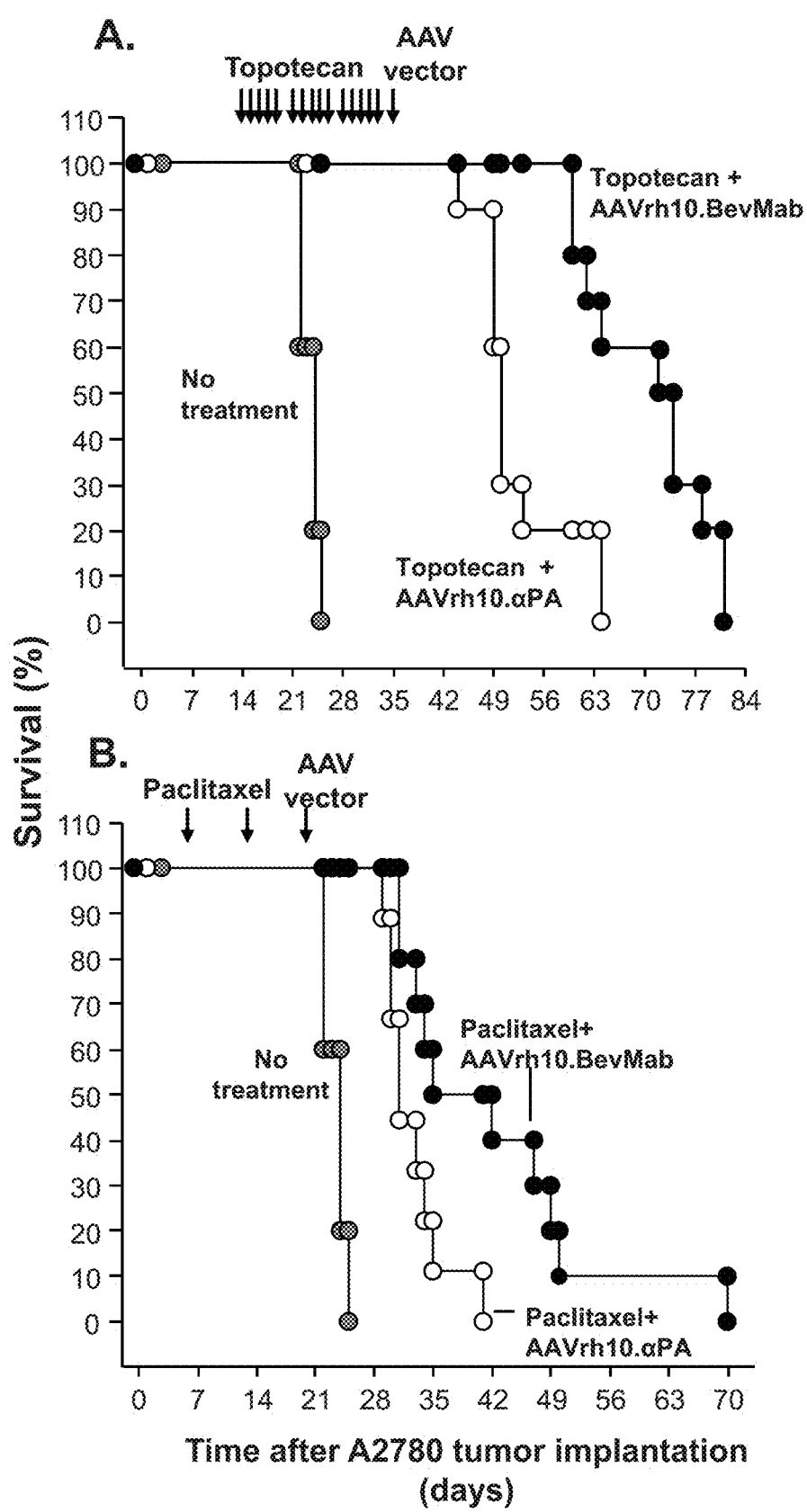

FIG. 6 depicts the results of experiments analyzing the effect of AAVrh10.BevMab on A2780 ovarian cancer cell tumor bearing mice pretreated with cytotoxic reagents. Panel A of FIG. 6 is a graph of the survival over time of mice pre-treated with topotecan followed by AAVrh10.BevMab or AAVrh10.αPA vector. Two weeks after ovarian cancer cell inoculation, topotecan was intraperitoneally injected into mice at 0.625 mg/kg-day, 5 days/week for 3 weeks. Five weeks after tumor cell inoculation, mice were administered intraperitoneally with $10^{11}$gc AAVrh10.BevMab or AAVrh10.αPA control vector. As a control, one group received no treatment. Survival is presented as the percentage of surviving mice in each group. Data were obtained from n=10 animals per group, p<0.001. Panel B of FIG. 6 is a graph illustrating the survival of mice pre-treated with paclitaxel followed by AAVrh10.BevMab or AAVrh10.αPA. One week after ovarian cancer cell inoculation, paclitaxel was intraperitoneally injected into mice at 20 mg/kg, once a week for 2 weeks; 3 weeks after tumor cell inoculation, mice were administered intraperitoneally with $10^{11}$ gc AAVrh10.BevMab or AAVrh10.αPA control vector. As a control, one group received no treatment. Survival is presented as the percentage of surviving mice in each group. Data were obtained from n=9-10 animals per group, AAVrh10.BevMab vs. no treatment, p<0.0001, AVrh.10BevMab vs. AAVrh10.αPA, p=0.01.

DETAILED DESCRIPTION OF THE INVENTION

The inventive method comprises administering a composition comprising an adeno-associated virus (AAV) vector which comprises a nucleic acid sequence encoding an anti-VEGF antibody or an antigen-binding fragment thereof. A single administration of an AAV vector expressing bevacizumab desirably results in sustained expression of bevacizumab at levels sufficient for long-term treatment of ovarian cancer with minimal adverse events.

Adeno-associated virus is a member of the Parvoviridae family and comprises a linear, single-stranded DNA genome of less than about 5,000 nucleotides. AAV requires co-infection with a helper virus (i.e., an adenovirus or a herpes virus), or expression of helper genes, for efficient replication. AAV vectors used for administration of therapeutic nucleic acids have approximately 96% of the parental genome deleted, such that only the terminal repeats (ITRs), which contain recognition signals for DNA replication and packaging, remain. This eliminates immunologic or toxic side effects due to expression of viral genes. In addition, delivering specific AAV proteins to producing cells enables integration of the AAV vector comprising AAV ITRs into a specific region of the cellular genome, if desired (see, e.g., U.S. Pat. Nos. 6,342,390 and 6,821,511). Host cells comprising an integrated AAV genome show no change in cell growth or morphology (see, for example, U.S. Pat. No. 4,797,368).

The AAV ITRs flank the unique coding nucleotide sequences for the non-structural replication (Rep) proteins and the structural capsid (Cap) proteins (also known as virion proteins (VPs)). The terminal 145 nucleotides are self-complementary and are organized so that an energetically stable intramolecular duplex forming a T-shaped hairpin may be formed. These hairpin structures function as an origin for viral DNA replication by serving as primers for the cellular DNA polymerase complex. The Rep genes encode the Rep proteins Rep78, Rep68, Rep52, and Rep40. Rep78 and Rep68 are transcribed from the p5 promoter, and Rep52 and Rep40 are transcribed from the p19 promoter. The Rep78 and Rep68 proteins are multifunctional DNA binding proteins that perform helicase and nickase functions during productive replication to allow for the resolution of AAV termini (see, e.g., Im et al., *Cell*, 61: 447-57 (1990)). These proteins also regulate transcription from endogenous AAV promoters and promoters within helper viruses (see, e.g., Pereira et al., *J. Viral.*, 71: 1079-1088 (1997)). The other Rep proteins modify the function of Rep78 and Rep68. The cap genes encode the capsid proteins VP1, VP2, and VP3. The cap genes are transcribed from the p40 promoter.

The AAV vector used in the inventive method can be generated using any AAV serotype known in the art. Several AAV serotypes and over 100 AAV variants have been isolated from adenovirus stocks or from human or nonhuman primate tissues (reviewed in, e.g., Wu et al., *Molecular Therapy*, 14(3): 316-327 (2006)). Generally, the AAV serotypes have genomic sequences of significant homology at the nucleic acid sequence and amino acid sequence levels, such that different serotypes have an identical set of genetic functions, produce virions which are essentially physically and functionally equivalent, and replicate and assemble by practically identical mechanisms. AAV serotypes 1-6 and 7-9 are defined as "true" serotypes, in that they do not efficiently cross-react with neutralizing sera specific for all other existing and characterized serotypes. In contrast, AAV serotypes 6, 10 (also referred to as Rh 10), and 11 are considered "variant" serotypes as they do not adhere to the definition of a "true" serotype. AAV serotype 2 (AAV2) has been used extensively for gene therapy applications due to its lack of pathogenicity, wide range of infectivity, and ability to establish long-term transgene expression (see, e.g., Carter, B. J., *Hum. Gene Ther.,* 16: 541-550 (2005); and Wu et al., supra). Genome sequences of various AAV serotypes and comparisons thereof are disclosed in, for example, GenBank Accession numbers U89790, J01901, AF043303, and AF085716; Chiorini et al., *J. Virol.,* 71: 6823-33 (1997); Srivastava et al., *J. Virol.,* 45: 555-64 (1983); Chiorini et al., *J. Virol.,* 73: 1309-1319 (1999); Rutledge et al., *J. Virol.,* 72: 309-319 (1998); and Wu et al., *J. Virol.,* 74: 8635-47 (2000)).

AAV rep and ITR sequences are particularly conserved across most AAV serotypes. For example, the Rep78 proteins of AAV2, AAV3A, AAV3B, AAV4, and AAV6 are reportedly about 89-93% identical (see Bantel-Schaal et al., *J. Virol.,* 73(2): 939-947 (1999)). It has been reported that AAV serotypes 2, 3A, 3B, and 6 share about 82% total nucleotide sequence identity at the genome level (Bantel-Schaal et al., supra). Moreover, the rep sequences and ITRs of many AAV serotypes are known to efficiently cross-complement (i.e., functionally substitute) corresponding sequences from other serotypes during production of AAV particles in mammalian cells.

Generally, the cap proteins, which determine the cellular tropicity of the AAV particle, and related cap protein-encoding sequences, are significantly less conserved than Rep genes across different AAV serotypes. In view of the ability Rep and ITR sequences to cross-complement corresponding sequences of other serotypes, the AAV vector can comprise a mixture of serotypes and thereby be a "chimeric" or "pseudotyped" AAV vector. A chimeric AAV vector typically comprises AAV capsid proteins derived from two or more (e.g., 2, 3, 4, etc.) different AAV serotypes. In contrast, a pseudotyped AAV vector comprises one or more ITRs of one AAV serotype packaged into a capsid of another AAV serotype. Chimeric and pseudotyped AAV vectors are further described in, for example, U.S. Pat. No. 6,723,551; Flotte, *Mol. Ther.,* 13(1): 1-2 (2006), Gao et al., *J. Virol.,* 78: 6381-6388 (2004), Gao et al., *Proc. Natl. Acad. Sci. USA,* 99: 11854-11859 (2002), De et al., *Mol. Ther.,* 13: 67-76 (2006), and Gao et al., *Mol. Ther.,* 13: 77-87 (2006).

In one embodiment, the AAV vector is generated using an AAV that infects humans (e.g., AAV2). Alternatively, the AAV vector is generated using an AAV that infects non-human primates, such as, for example, the great apes (e.g., chimpanzees), Old World monkeys (e.g., macaques), and New World monkeys (e.g., marmosets). Preferably, the AAV vector is generated using an AAV that infects a non-human primate pseudotyped with an AAV that infects humans. Examples of such pseudotyped AAV vectors are disclosed in, e.g., Cearley et al., *Molecular Therapy,* 13: 528-537 (2006). In one embodiment, an AAV vector can be generated which comprises a capsid protein from an AAV that infects rhesus macaques pseudotyped with AAV2 inverted terminal repeats (ITRs). In a particularly preferred embodiment, the AAV vector of the inventive method comprises a capsid protein from AAV10 (also referred to as "AAVrh.10"), which infects rhesus macaques pseudotyped with AAV2 ITRs (see, e.g., Watanabe et al., *Gene Ther.,* 17(8): 1042-1051 (2010); and Mao et al., *Hum. Gene Therapy,* 22: 1525-1535 (2011)).

The AAV vector of the inventive method comprises a nucleic acid sequence encoding an anti-VEGF antibody or an antigen-binding fragment thereof. "Nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to methylated and/or capped polynucleotides.

One of ordinary skill in the art will appreciate that an antibody consists of four polypeptides: two heavy (H) chain polypeptides and two light (L) chain polypeptides. Each of the heavy chains contains one N-terminal variable ($V_H$) region and three C-terminal constant ($C_H1$, $C_H2$ and $C_H3$) regions, and each light chain contains one N-terminal variable ($V_L$) region and one C-terminal constant ($C_L$) region. The variable regions of each pair of light and heavy chains form the antigen binding site of an antibody. The AAV vector of the inventive method can comprise one or more nucleic acid sequences, each of which encodes one or more of the heavy and/or light chain polypeptides of an anti-VEGF antibody. In this respect, the AAV vector of the inventive method can comprise a single nucleic acid sequence that encodes the two heavy chain polypeptides and the two light chain polypeptides of an anti-VEGF antibody. Alternatively, the AAV vector of the inventive method can comprise a first nucleic acid sequence that encodes both heavy chain polypeptides of an anti-VEGF antibody, and a second nucleic acid sequence that encodes both light chain polypeptides of an anti-VEGF antibody. In yet another embodiment, the AAV vector can comprise a first nucleic acid sequence encoding a first heavy chain polypeptide of an anti-VEGF antibody, a second nucleic acid sequence encoding a second heavy chain polypeptide of an anti-VEGF antibody, a third nucleic acid sequence encoding a first light chain polypeptide of an anti-VEGF antibody, and a fourth nucleic acid sequence encoding a second light chain polypeptide of an anti-VEGF antibody.

The AAV vector of the inventive method can comprise a nucleic acid sequence encoding full-length heavy and light chain polypeptides of any anti-VEGF antibody known in the art. In a preferred embodiment the AAV vector comprises a nucleic acid sequence encoding the anti-VEGF antibody bevacizumab, or antigen-binding fragment thereof.

Bevacizumab (AVASTIN™, Genenetch, Inc., South San Francisco, Calif.) is a humanized monoclonal antibody that inhibits vascular endothelial growth factor A (VEGF-A) (Ferrara et al., *Nat. Rev. Drug Discov.,* 3(5): 391-400 (2004); Avery et al., *Ophthalmology,* 113: 363-372 (2006), and U.S. Pat. No. 6,884,879). Nucleic acid sequences encoding the full-length heavy and light chain polypeptides of bevacizumab are known in the art (see, e.g., Watanabe et al., supra, Mao et al., supra, and U.S. Pat. No. 6,884,879) and include, for example, SEQ ID NO: 1 and SEQ ID NO: 2, respectively. The AAV vector of the inventive method can comprise a nucleic acid sequence encoding a whole anti-VEGF antibody (e.g., bevacizumab), such as, for example, SEQ ID NO: 3. In another embodiment, the AAV vector can comprise a nucleic acid sequence that encodes an antigen-binding fragment (also referred to as an "antibody fragment") of any anti-VEGF antibody known in the art (e.g. antigen binding fragment of bevacizumab).

The term "antigen-binding fragment," refers to one or more fragments of an antibody that retain the ability to specifically bind to an antigen (e.g., VEGF) (see, generally, Holliger et al., *Nat. Biotech.*, 23(9): 1126-1129 (2005)). Examples of antigen-binding fragments include but are not limited to (i) a Fab fragment, which is a monovalent fragment consisting of the $V_L$, $V_H$, $C_L$, and $C_H1$ domains; (ii) a F(ab')$_2$ fragment, which is a bivalent fragment comprising two Fab fragments linked by a disulfide bridge at the hinge region; and (iii) a Fv fragment consisting of the $V_L$ and $V_H$ domains of a single arm of an antibody. In one embodiment, the AAV vector can comprise a nucleic acid sequence encoding a Fab fragment of bevacizumab. An example of a Fab fragment of bevacizumab is ranibizumab (LUCENTIS™, Genentech, Inc., South San Francisco, Calif.), which is derived from the same parent molecule of bevacizumab. Nucleic acid sequences encoding Fab fragments of bevacizumab are known in the art and are disclosed in, for example, Chen et al., *Cancer Research*, 57: 4593-4599 (1997), and U.S. Pat. No. 6,884,879.

The nucleic acid sequence encoding an anti-VEGF antibody or an antigen-binding fragment thereof, can be generated using methods known in the art. For example, nucleic acid sequences, polypeptides, and proteins can be recombinantly produced using standard recombinant DNA methodology (see, e.g., Sambrook et al., *Molecular Cloning: A Laboratory Manual*, 3$^{rd}$ ed., Cold Spring Harbor Press, Cold Spring Harbor, N.Y., 2001; and Ausubel et al., *Current Protocols in Molecular Biology*, Greene Publishing Associates and John Wiley & Sons, NY, 1994). Further, a synthetically produced nucleic acid sequence encoding an anti-VEGF antibody or an antigen-binding fragment thereof, can be isolated and/or purified from a source, such as a bacterium, an insect, or a mammal, e.g., a rat, a human, etc. Methods of isolation and purification are well-known in the art. Alternatively, the nucleic acid sequences described herein can be commercially synthesized. In this respect, the nucleic acid sequence can be synthetic, recombinant, isolated, and/or purified.

In addition to the nucleic acid sequence encoding an anti-VEGF antibody or an antigen-binding fragment thereof, the AAV vector preferably comprises expression control sequences, such as promoters, enhancers, polyadenylation signals, transcription terminators, internal ribosome entry sites (IRES), and the like, that provide for the expression of the nucleic acid sequence in a host cell. Exemplary expression control sequences are known in the art and described in, for example, Goeddel, *Gene Expression Technology: Methods in Enzymology*, Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, and the RSV promoter. Inducible promoters include, for example, the Tet system (U.S. Pat. Nos. 5,464,758 and 5,814,618), the Ecdysone inducible system (No et al., *Proc. Natl. Acad. Sci.*, 93: 3346-3351 (1996)), the T-REX™ system (Invitrogen, Carlsbad, Calif.), LACSWITCH™ System (Stratagene, San Diego, Calif.), and the Cre-ERT tamoxifen inducible recombinase system (Indra et al., *Nuc. Acid. Res.*, 27: 4324-4327 (1999); *Nuc. Acid. Res.*, 28: e99 (2000); U.S. Pat. No. 7,112,715; and Kramer & Fussenegger, *Methods Mol. Biol.*, 308: 123-144 (2005)).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. In one embodiment, the nucleic acid sequence encoding bevacizumab or an antigen-binding fragment thereof is operably linked to a CMV enhancer/chicken β-actin promoter (see, e.g., Niwa et al., *Gene*, 108: 193-199 (1991); Daly et al., *Proc. Natl. Acad. Sci. U.S.A.*, 96: 2296-2300 (1999); and Sondhi et al., *Mol. Ther.*, 15: 481-491 (2007)).

The inventive method comprises administering to a patient the above-described AAV vector for the treatment of ovarian cancer. The AAV vector may be administered alone or as part of a composition comprising the AAV vector and a pharmaceutically acceptable (e.g. physiologically acceptable) carrier. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., *Remington: The Science and Practice of Pharmacy*, 21st Edition, Lippincott Williams & Wilkins, Philadelphia, Pa. (2001).

The AAV vector may be administered by any route as long as the AAV vector expresses the anti-VEGF antibody or antigen binding fragment thereof and treats ovarian cancer. The AAV vector can be administered, for example, intraorally, intramuscularly, transdermally, intravenously, intraarterially, subcutaneously, intradermally, and intraperitoneally. In a preferred embodiment, the AAV vector encoding an anti-VEGF antibody or antigen binding fragment thereof is administered intraperitoneally by intraperitoneal injection.

The AAV vector may be administered multiple times during a therapeutic or prophylactic treatment period and/or employ multiple administration routes, e.g., intramuscular and subcutaneous, to ensure sufficient exposure of cells to the composition. For example, the composition may be administered to the mammal two or more times (e.g., 2, 3, 4, 5, 6, 6, 8, 9, or 10 or more times) during a therapeutic or prophylactic treatment period. Desirably, however, a single administration of the AAV vector to a patient results in the patient producing a therapeutically effect amount of an anti-VEGF antibody or antigen binding fragment thereof for an extended period of time (e.g., about 15 days or more, about 30 days or more, about 60 days or more, about 75 days or more, about 90 days or more, about 4 months or more, about 6 months or more, about 10 months or more, or even about 12 months or more).

Thus, in preferred aspects, the above described AAV vector need not be repeatedly administered to sustain therapeutic dosages over an extended time frame. In some embodiments of the method, the AAV vector is administered to the patient not more than once within about 30 days, not more than once within about 45 days, not more than once within about 60 days, not more than once within about 75 days, or even not more than once within about 90 days (e.g., not more than once within about 4 months, about 5 months, about 6 months, about 10 months, or about 12 months).

The inventive method is used to treat ovarian cancer in a patient, preferably a human. As used herein, the terms "treatment," "treating," and the like refer to obtaining a desired pharmacologic and/or physiologic effect, e.g., partially or completely cures a disease or an adverse symptom attributable to a disease (e.g., inhibiting ovarian cancer growth or metastasis). To this end, the inventive method can include administering a "therapeutically effective amount" of the AAV vector encoding an anti-VEGF or antigen binding fragment thereof described herein.

A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the AAV vector encoding an anti-VEGF or antigen binding fragment to elicit a desired response in the individual. The dose of AAV vector required to achieve a particular therapeutic effect (i.e., inhibiting ovarian cancer growth or metastasis) typically is administered in units of vector genome copies per cell (gc/cell) or vector genome copies/per kilogram of body weight (gc/kg), and this dose will vary based on several factors including, but not limited to, the administration route of the composition, the level of gene expression required to achieve a therapeutic effect, the specific disease or disorder being treated, any host immune response to the AAV vector, and the stability of the anti-VEGF antibody or antigen binding fragment thereof in the patient. One of ordinary skill in the art can readily determine an appropriate AAV vector dose range to treat a patient having a particular ocular disease or disorder based on these and other factors that are well known in the art.

Alternatively, the pharmacologic and/or physiologic effect may be prophylactic, i.e., the effect completely or partially prevents ovarian cancer in a patient that is susceptible (e.g., genetic predisposition) for the development of ovarian cancer. In this respect, the inventive method comprises administering a "prophylactically effective amount" of the AAV vector encoding an anti-VEGF or antigen binding fragment described herein to a human that is predisposed to, or otherwise at risk of developing, ovarian cancer. A "prophylactically effective amount" refers to an amount effective, at dosages and for periods of time necessary, to achieve a desired prophylactic result (e.g., prevention of disease onset or prevention of disease flare-ups).

In one embodiment, the inventive method further comprises administering a chemotherapeutic agent with the AAV vector encoding an anti-VEGF antibody or antigen binding fragment. Any chemotherapeutic agents approved for the treatment of ovarian cancer known in the art may be used in the inventive method. Examples of therapeutic agents approved for the treatment of ovarian cancer include, but are not limited to, cisplatin, doxorubicin, cyclophosphamide, topotecan, carboplatin, and paclitaxel. The chemotherapeutic agent and AAV vector can be administered simultaneously or sequentially in any order. In one embodiment, the chemotherapeutic agent is administered to the patient prior to the administration of the AAV vector encoding an anti-VEGF or antigen binding fragment. For example, a patient may receive an entire scheduled cycle of the chemotherapeutic agent prior to the administration of the AAV vector encoding an anti-VEGF or antigen binding fragment. Alternatively, the AAV vector encoding an anti-VEGF or antigen binding fragment may be administered 1, 2, 3, 4, 5, 6, 7, 8, 9, or 10 weeks after the first administration of a chemotherapeutic agent in a chemotherapeutic cycle.

The following examples further illustrate the invention but, of course, should not be construed as in any way limiting its scope.

Example 1

This example demonstrates the local expression of an anti-VEGF antibody in the peritoneal cavity following intraperitoneal (IP) or intravenous (IV) injection.

AAVrh.10 is a clade E, nonhuman primate (rhesus macaque)-derived gene-transfer vector that has been used in human clinical trials for gene therapy for CNS hereditary disease (Sondhi et al., supra). A bevacizumab-encoding AAV vector, AAVrh.10BevMab, was designed based on the AAVrh.10 capsid pseudotyped with AAV2 inverted terminal repeats (ITRs). The ITRs flanked an expression cassette containing (i) the cytomegalovirus (CMV)-enhancer chicken β-actin promoter (Niwa et al., *Gene,* 108: 193-199 (1991); Daly et al., *Proc. Natl. Acad. Sci. U.S.A.,* 96: 2296-2300 (1999); and Sondhi et al., supra), (ii) nucleic acid sequences encoding the bevacizumab heavy and light chains separated by a furin 2A self cleavage site (Fang et al., *Nat. Biotechnol.,* 23: 584-590 (2005)), and (iii) the rabbit α-globin polyadenylation signal.

AAV vectors were produced using 2 plasmids: (1) an expression cassette plasmid pAAVαVEGF or pAAVαPA carrying the transgene (humanized anti-human VEGF antibody cDNA for pAAVαVEGF, anti-anthrax protective antigen antibody cDNA for pAAVαPA; and (2) pPAK helper plasmid. To produce the AAVrh.10 vectors, pAAVαVEGF or pAAVαPA (600 μg) and pPAK helper plasmid (1200 μg) were co-transfected into human embryonic kidney 293T cells in 40 150 mm petri-dish using PEI"max". Seventy-two hours after transfection, cells were harvested and a crude viral lysate was prepared using 5 cycles of freeze/thaw followed by centrifugation. The AAV vector was purified by iodixanol gradient and QHP anion exchange chromatography. He purified AAV vector was concentrated using a centrifuge filter device and stored in phosphate buffered saline (PBS, pH=7.4) at −80° C. Vector genome titers were determined by quantitative PCR using a chicken β-actin promoter specific primer-probe set.

Peritoneal cavity expression of the anti-VEGF antibody bevacizumab was assessed following IP or IV injection of an AAV vector encoding the anti-VEGF antibody bevacizumab, AAVrh.10BevMab (see, U.S. Patent Application Publication 2013/0090375). AAVrh10.BevMab ($10^{11}$ gc) in 200 μl PBS was administered intraperitoneally or intravenously to 14 to 15 week old female Balb/c mice. After 9 weeks, peritoneal lavage was carried out with 1 ml PBS and omentum, mesentery and diaphragm were collected. Protein in tissue was extracted by homogenizing 10 mg of tissue in 200 μl of T-PER® tissue protein extraction reagent (Thermo Scientific, Rockford, Ill.). The levels of bevacizumab in lavage, tissue and organs were determined by a human VEGF-specific enzyme-linked immunosorbent assay (ELISA) as previously described with minor modifications (see, Mao et al., *Hum Gene Ther*, 22: 1525-1535 (2011)). Flat-bottomed 96-well EIA/RIA plates (Corning Life Sciences, Lowell, Mass.) were coated with 0.02 µg human VEGF-A165 (R&D Systems, Minneapolis, Minn.) per well in a total volume of 100 µl of 0.05 M carbonate buffer overnight at 4° C. The plates were washed three times with PBS and blocked with 5% dry milk in PBS for 30 min. The plates were washed 3 times with PBS containing 0.05% Tween-20 (Bio-Rad Laboratories, Hercules, Calif.). Serial dilution of lavage or tissue protein lysates in PBS containing 1% dry milk were added to each well and incubated for 60 min at room temperature. Bevacizumab (Genentech, San Francisco, Calif.) was used as standard. The plates were washed three times with PBS/Tween-20, and then 100 µl/well of 1:5000 diluted peroxidase conjugated goat anti-human kappa light chain (Sigma-Aldrich) in PBS containing 1% dry milk was added and incubated for 60 min, 23° C. The plates were washed four times with PBS/Tween-20 and once with PBS. Peroxidase substrate (100 µl/well, Bio-Rad, Hercules, Calif.) was added. After 15 min, the reaction was stopped by addition of 100 µl/well of 2% oxalic acid (Sigma-Aldrich). Absorbance at 415 nm was measured. Bevacizumab concentrations were calculated according to the standard curve based on a log (OD)-log (concentration) interpolation model and a cutoff value equal to 2-fold the absorbance of background. Bevacizumab expression was standardized by total protein concentration using a bicinchoninic acid assay (Bio-Rad) following the manufacturer's instructions.

The results of the ELISA assay are shown in FIG. 1. Bevacizumab expression was detected in the lavage, omentum, mesentery, and diaphragm samples for both IP and IV injection. IP injection showed increased bevacizumab expression compared to IV injection for each of the peritoneal samples tested.

The results of this example confirm that a single administration of an AAV vector encoding an anti-VEGF antibody or antigen binding fragment thereof provides persistent expression of antibody in the peritoneal cavity.

Example 2

This example demonstrates a method of treating ovarian cancer comprising administering an AAV vector encoding an anti-VEGF antibody.

The effect of administration of AAVrh10.BevMab on tumor growth of ovarian cancer was established in a mouse model of ovarian cancer. Xenografts of human ovarian cancer cells were established by administering 5 million A2780 ovarian cancer cells intraperitoneally in 6 to 8 week old female Balb/c nude mice. One day after tumor cell inoculation, the mice were injected intraperitoneally with $10^{11}$ gc AAVrh10.BevMab or an AAVrh10. vector encoding an irrelevant IgG antibody (AAVrh10.αPA). Mice were sacrificed at different time points for tumor burden measurement. Quantitative TaqMan real-time PCR analysis for Alu was used to quantify human DNA as tumor burden in ovarian cancer mouse xenografts (see e.g., Watanabe et al., *Gene Ther.*, 17: 1042-1051 (2010)). Genomic DNA from mouse tissue was extracted with a DNeasy Blood & Tissue Kit (Qiagen, Valencia, Calif.) and quantified by Nanodrop (Qiagen). All genomic DNA samples were diluted to a working concentration of 1 ng/µl and 1 µl of genomic DNA was amplified. Human DNA standard series containing 0.01, 0.1, and 1 ng of human DNA per microliter was prepared with mouse DNA to make the total DNA concentration 1 ng/µl. The following primer-probe sets specific to human Alu coding sequence were used: Alu-P1 5'-CGGGTT-CACGCCATTCTC-3' and Alu-P2 5'-AAAAATT-AGCCGGGCGTAGTG-3' and Alu Probe 5'FAM-AGCTGGGACTACAGGCGCCCG-TAMRA 3'. The amount of human DNA in tumor tissue was normalized per total DNA.

Treatment with AAVrh10.BevMab resulted in a marked reduction of peritoneal carcinomatosis of ovarian cancer measured at day 24, as shown in FIG. 2A. Tumor weight and A2780-derived human DNA were measured on days 14, 21 and 24. On day 14, AAVrh10.αPA-treated mice showed detectable tumor growth, whereas the AAVrh.10BevMab treated-mice had no visually detectable tumors (control 0.11±0.8 g vs. treated not detectable). By day 21, the difference was 55-fold greater tumor weight in the control group (control 1.1±0.7 g vs. treated 0.02±0.01 g, p b 10–3) and on day 24, the difference was 15-fold (control 2.2±0.6 g vs. treated 0.15±0.2, p b 10–7), as shown in FIG. 2B. Tumor burden was also quantified by quantitative PCR for the tumor-derived human DNA in tissue in mouse peritoneal cavity. In the control vector-treated group, human DNA accounted for 8, 35 and 42% of the total DNA (from both mouse and human) on days 14, 21, and 24, respectively, whereas in the AAVrh10.BevMab-treated group, human DNA was only 1, 3 and 10% on days 14, 21 and 24, respectively, as shown in FIG. 2C.

The results of this example confirm that treatment with an AAV vector encoding an anti-VEGF antibody significantly slows tumor growth in the peritoneal cavity.

Example 3

This example demonstrates the effect of administering an AAV vector encoding an anti-VEGF antibody on angiogenesis of ovarian cancer.

The effect of administration of AAVrh10.BevMab on angiogenesis of ovarian cancer was established in a mouse model of ovarian cancer. Xenografts of human ovarian cancer cells were established by administering 5 million A2780 ovarian cancer cells intraperitoneally in 6 to 8 week old female Balb/c nude mice. One day after tumor cell inoculation, the mice were administered $10^{11}$ gc AAVrh10.BevMab, an AAVrh10. vector encoding an irrelevant IgG antibody (AAVrh10.αPA), or PBS injected intraperitoneally. On day 24, tumor nodules were collected and embedded into optimum cutting temperature compound (Sakura Finetek, Torrance, Calif.). Tissue sections were stained with rat polyclonal antibodies against mouse CD31 (Abcam, Cambridge, Mass.). Sections were incubated in a blocking solution (PBS containing 10% normal goat serum and 2% bovine serum albumin) for 1 h, 23° C. Primary antibody diluted with blocking solution (1:300) was applied to the sections and incubated overnight at 4° C. After washing with PBS, the slides were incubated with a secondary antibody, goat anti-rat IgG conjugated with cy3 (Invitrogen, Eugene, Oreg.) diluted with blocking buffer (1:1000) for 2 h, 23° C. After 3 washes, sections were mounted with prolong gold anti-fade reagent with DAPI (Invitrogen, Eugene, Oreg.). Sections were examined with an Olympus IX71 microscope, and representative areas were photographed using a 20× objective. Five fields from each section containing the highest frequency of blood vessels were examined. The quantification of vascular area was analyzed using ImageScope (Aperio, Vista, Calif.).

The results in FIG. 3A show a significant reduction of vasculature, visualized by a decrease in CD31+ tumors, in AAVrh10.BevMab-treated tumors as compared with PBS-, and AAVrh10.αPA-treated tumors. Quantification of blood vessel area, shown in FIG. 3B, revealed that blood vessels accounted for 0.63% tumor area in AAVrh10.BevMab-treated tumors, while there was 4.6-fold and 5.3-fold more vasculature in tumors treated with PBS or AAVrh10.αPA, respectively.

The results of this example demonstrate that administration of an AAV vector encoding an anti-VEGF antibody reduces the angiogenesis of ovarian cancer.

Example 4

This example demonstrates the effect of administering an AAV vector encoding an anti-VEGF antibody on survival in a mouse model of ovarian cancer.

Xenografts of human ovarian cancer cells were established by administering 5 million A2780 ovarian cancer cells or SK-OV3 ovarian cancer cells intraperitoneally in 6 to 8 week old female Balb/c nude mice. One day after tumor cell inoculation, the mice were administered $10^{11}$ gc AAVrh10.BevMab, an AAVrh10. vector encoding an irrelevant IgG antibody (AAVrh10.αPA), or PBS injected intraperitoneally. Survival is presented as the percentage of surviving mice in each group.

The results of these survival studies are shown in FIGS. 4A (A2780 ovarian cancer cell xenografts) and 4B (SK-OV3 ovarian cancer cell xenografts). AAVrh10.BevMab treatment significantly increased survival of mice with A2780 tumors ($p<0.0001$, AAVrh10.BevMab vs. all other groups) and SK-OV3 tumors ($p<0.001$, AAVrh10.BevMab vs. all other groups). The median survival days for mice with A2780 tumors are 24 days, 23 days and 39 days for mice treated with PBS, AAVrh10.αPA control and AAVrh10.BevMab, respectively.

The results of this example demonstrate that treatment of ovarian cancer with an AAV vector encoding an anti-VEGF antibody significantly increases survival.

Example 5

This example demonstrates the efficacy of treating established ovarian cancer tumors with an AAV vector encoding an anti-VEGF antibody Xenografts of human ovarian cancer cells were established by administering 2 million A2780-luciferase ovarian cancer cells intraperitoneally in 6 to 8 week old female Balb/c nude mice. The A2780-luciferase ovarian cancer cells are genetically modified and tagged with luciferase so that peritoneal dissemination of the ovarian cancer could be evaluated by in vivo imaging. Four days after tumor cell inoculation, the mice were administered $10^{11}$ gc AAVrh10.BevMab or an AAVrh10. vector encoding an irrelevant IgG antibody (AAVrh10.αPA) injected intraperitoneally. The mice were analyzed for changes in tumor growth, measured by luciferase activity, and survival. In vivo luciferase activity was measured with Xenogen IVIS imaging system (Xenogen, Alameda, Calif.) composed of a charge-coupled device connected to a light-tight black chamber. Mice with A2780-Luciferase xenografts were injected intraperitoneally with d-luciferin (Caliper Life Sciences, Hopkinton, Mass.) in PBS at a dose of 150 mg/kg bodyweight and anesthetized with 2.5% isoflurane (Piramal Healthcare, Andhra Pradesh, India). Mice were placed prone in the chamber. Fifteen minutes after d-luciferin injection, bioluminescence images were taken and gray scale reference images were obtained under dim illumination. Pseudocolor images representing bioluminescent intensity were acquired with LivingImage software (Caliper Life Sciences, Hopkinton, Mass.). These images were superimposed on the gray scale images for analysis with LivingImage 3.2. The data were expressed as photo emission (photons/s-cm2 steradian).

The results, shown in FIG. 5, indicate that there was no difference in luciferase expression between AAVrh10.BevMab-treated mice and control vector-treated mice until 14 days after tumor cell implantation (FIGS. 5A and 5B). On day 14, there was significantly higher luciferase expression in the AAVrh10.αPA-treated control group than in the AAVrh10.BevMab-treated group, indicating higher tumor burden in the control group (FIGS. 5A and 5B). Consistent with the imaging data, AAVrh10.BevMab-treated mice exhibited a statistically significant survival advantage in contrast to mice that received the AAVrh10.αPA control vector, as shown in FIG. 5C ($p<0.0001$).

The results from this example demonstrate that an AAV vector encoding an anti-VEGF antibody can be used to treat patients with established ovarian cancer.

Example 6

This example demonstrates increased survival in animals treated with a chemotherapeutic agent and an AAV vector encoding an anti-VEGF antibody.

Xenografts of human ovarian cancer cells were established by administering 5 million A2780 ovarian cancer cells intraperitoneally in 6 to 8 week old female Balb/c nude mice. Survival was analyzed in the mice which were either left untreated, treated with the chemotherapeutic topotecan in combination with an AAV vector, or treated with the chemotherapeutic paclitaxel in combination with an AAV vector. To establish the topotecan-AAVrh. 10BevMab combination treatment model, 2 weeks after injection of the A2780 ovarian cancer cells, the mice were treated with topotecan at 0.625 mg/kg body weight/day, 5 times/week for 3 weeks (see, Delord et al., *Ann. Oncol.*, 16: 1889-1897 (2005)). Five weeks after tumor cell inoculation, AAVrh10.BevMab or AAVrh10.α-PA ($10^{11}$gc in 200 µl of PBS) was administered intraperitoneally. To establish the paclitaxel-AAVrh.10BevMab combination treatment model, 1 week after injection of the A2780 ovarian cancer cells, the mice were treated with paclitaxel at 20 mg/kg body weight, once/week for 2 weeks (see, Vassileva et al., *Mol Cancer Ther.*, 7: 630-637 (2008)). Three weeks after tumor cell inoculation, AAVrh10.BevMab or AAVrh10.α-PA ($10^{11}$gc in 200 µl of PBS) was administered intraperitoneally.

The results of these studies, shown in FIG. 6, demonstrate that at the doses and schedules used, topotecan and paclitaxel were efficacious as single agents, but the addition of the AAV vector coding for bevacizumab further prolonged survival of the ovarian cancer-bearing mice. The median survival was 24 days for mice without treatment. Topotecan treatment prolonged the median survival to 50 days, and the combination of topotecan and AAVrh10.BevMab treatment increased the median survival to 73 days, as shown in FIG. 6A. (topotecan+AAVrh10.BevMab vs. all other group, $p<0.001$). Mice receiving paclitaxel treatment only showed a median survival of 31 days, while addition of AAVrh10.BevMab increased it to 39 days, as shown in FIG.

6B. (paclitaxel+AAVrh10.BevMab vs. no treatment, p<0.0001, AAVrh10.BevMab vs. AAVrh10.αPA, p<0.02).

The results of this example demonstrate the feasibility of the combination of AAVrh10.BevMab with chemotherapy and the advantage of the addition of AAVrh10.BevMab to chemotherapy in ovarian cancer treatment.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating ovarian cancer in a patient, the method comprising administering to the patient:
   (a) paclitaxel and
   (b) a AAVrh10 vector comprising a promoter operably linked to a gene encoding bevacizumab,
   wherein the paclitaxel is administered to the patient prior to the administration of the AAVrh10 vector, and
   wherein the AAVrh10 vector is administered by intraperitoneal injection to the patient not more than once over a 30 day time period,
   thereby treating the ovarian cancer in the patient.

2. A method of treating ovarian cancer in a patient, the method comprising administering to the patient:
   (a) topetcan and
   (b) a AAVrh10 vector comprising a promoter operably linked to a gene encoding bevacizumab,
   wherein the topetcan is administered to the patient prior to the administration of the AAVrh10 vector, and
   wherein the AAVrh10 vector is administered by intraperitoneal injection to the patient not more than once over a 30 day time period,
   thereby treating the ovarian cancer in the patient.

* * * * *

UNITED STATES PATENT AND TRADEMARK OFFICE
CERTIFICATE OF CORRECTION

PATENT NO. : 10,946,094 B2
APPLICATION NO. : 15/052697
DATED : March 16, 2021
INVENTOR(S) : Ronald G. Crystal et al.

It is certified that error appears in the above-identified patent and that said Letters Patent is hereby corrected as shown below:

On the Title Page

Item (54) and in the Specification Column 1 Lines 1-3 title:
Delete: "ADENOASSOCIATED VIRAL MEDIATED PERSISTANT ANTI-VEGF THERAPY FOR OVARIAN CANCER"
And Insert: --ADENOASSOCIATED VIRAL MEDIATED PERSISTENT ANTI-VEGF THERAPY FOR OVARIAN CANCER--

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*